(12) United States Patent
Shirai

(10) Patent No.: US 6,673,224 B2
(45) Date of Patent: Jan. 6, 2004

(54) SEALING STRUCTURE OF GAS SENSOR

(75) Inventor: Makoto Shirai, Hekinan (JP)

(73) Assignee: Denso Corporation (JP)

( * ) Notice: Subject to any disclaimer, the term of this patent is extended or adjusted under 35 U.S.C. 154(b) by 44 days.

(21) Appl. No.: 09/877,126

(22) Filed: Jun. 11, 2001

(65) Prior Publication Data

US 2002/0014411 A1 Feb. 7, 2002

(30) Foreign Application Priority Data

Jun. 30, 2000 (JP) .......................................... 2000-198001
Apr. 20, 2001 (JP) .......................................... 2001-123091

(51) Int. Cl.[7] ............................................. G01N 27/407
(52) U.S. Cl. ........................ 204/427; 204/421; 204/428
(58) Field of Search ................................ 204/421–429

(56) References Cited

U.S. PATENT DOCUMENTS

| 2,937,100 | A |   | 5/1960  | Oldfield et al.   |
|-----------|---|---|---------|-------------------|
| 3,113,878 | A |   | 12/1963 | Martin            |
| 4,291,107 | A |   | 9/1981  | Barry et al.      |
| 4,691,142 | A |   | 9/1987  | Dohmen            |
| 5,179,047 | A |   | 1/1993  | Chiba             |
| 5,228,975 | A |   | 7/1993  | Yamada et al.     |
| 5,467,636 | A |   | 11/1995 | Thompson et al.   |
| 5,602,325 | A |   | 2/1997  | McClanahan et al. |
| 5,733,828 | A |   | 3/1998  | Usui et al.       |
| 5,739,414 | A |   | 4/1998  | Paulus et al.     |
| 5,785,829 | A | * | 7/1998  | Watanabe          |
| 6,347,543 | B1| * | 2/2002  | Geier et al.      |

FOREIGN PATENT DOCUMENTS

| DE | 19707456 A1 | 8/1998  |
|----|-------------|---------|
| DE | 19751424 A1 | 11/1998 |
| DE | 19850959 A1 | 5/2000  |
| EP | 0897897 A1  | 8/1997  |
| EP | 0932039 A2  | 7/1999  |
| JP | 2708915     | 10/1997 |
| JP | 2800883     | 7/1998  |
| JP | 2855096     | 11/1998 |
| JP | 11-513113   | 11/1999 |

* cited by examiner

Primary Examiner—T. Tung
(74) Attorney, Agent, or Firm—Nixon & Vanderhye PC

(57) ABSTRACT

An improved structure of a mechanical seal for keeping a gas chamber and a reference gas chamber airtight in a sensor body. A sensor element is disposed within an insulator. A gap between the sensor element and the insulator is sealed hermetically by a glass sealing member. The glass sealing member has a coefficient of thermal expansion whose differences between itself and the sensor element and the insulator is within a range of $\pm 3 \times 10^{-6}/°C$. This provides a mechanical seal required to keep the reference gas chamber and the gas chamber in the gas sensor airtight in an environment such as an automotive exhaust system subjected to a great temperature change.

13 Claims, 2 Drawing Sheets

SEALING STRUCTURE OF GAS SENSOR

BACKGROUND OF THE INVENTION

1. Technical Field of the Invention

Figure 1:
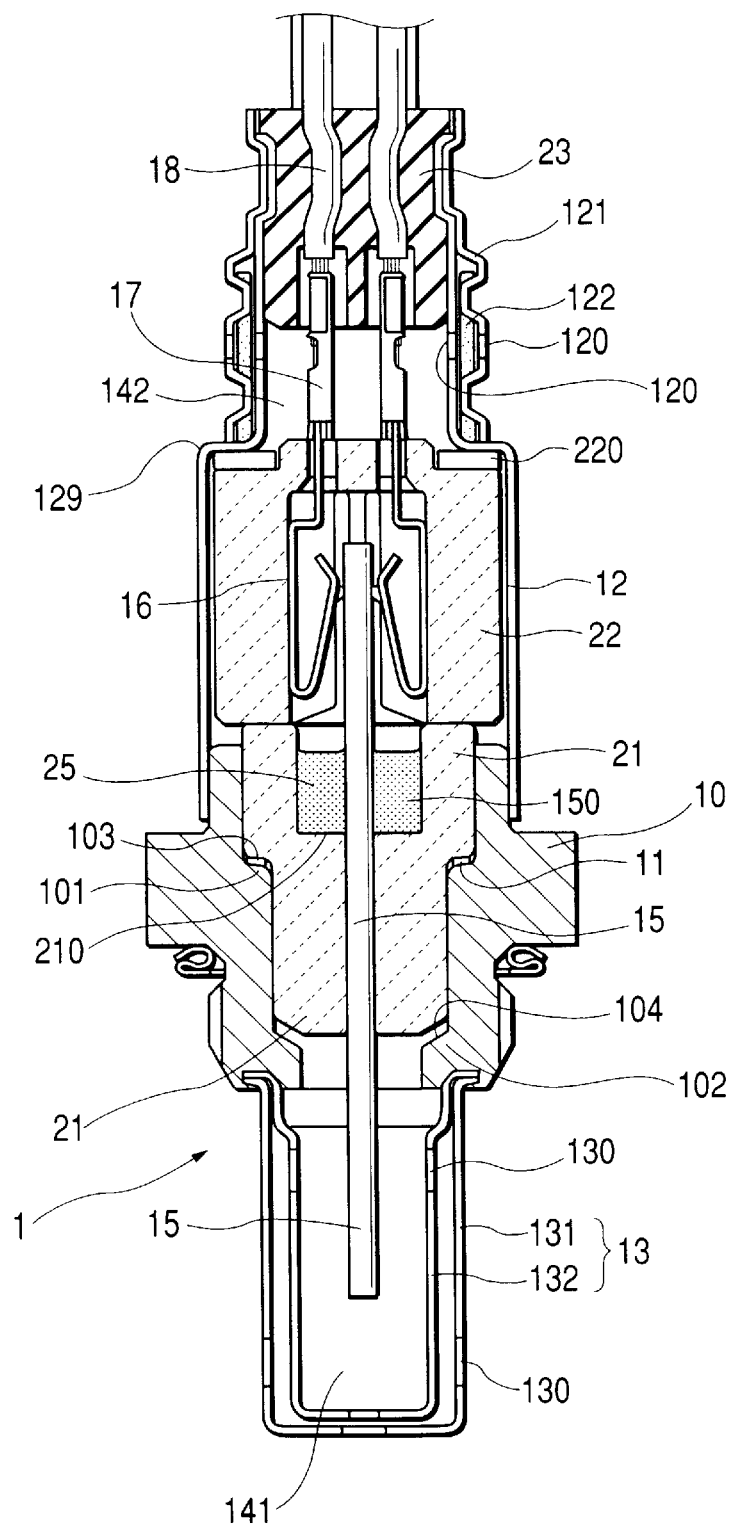

The present invention relates generally to a gas sensor which may be installed in an exhaust system of an internal combustion engine for air-fuel ratio control, and more particularly to an improved structure of a mechanical seal which keeps a reference gas chamber and a gas chamber airtight in a gas sensor.

2. Background Art

Gas sensors are know which are fabricated by inserting a sensor element into an insulation porcelain, mounting the insulation porcelain in a housing, installing a gas cover and an air cover on a front end and a base end of the housing, respectively, and sealing a gap between the insulation porcelain and the housing and a gap between the sensor element and the insulation porcelain hermetically. These seals define a measured gas chamber and an air chamber within the gas sensor in an airtight fashion.

The sensor element has a measuring electrode exposed to a gas to be measured and a reference electrode exposed to a reference gas or air and provides a signal in the form of an ion current flowing through the measuring and reference electrodes or a potential difference between the measuring and reference electrodes to determine the concentration of the gas. The leakage of the gas from the measured gas chamber to the air chamber or vice versa will, thus, result in a decrease in accuracy of measuring the concentration of the gas. In order to avoid this problem, typical gas sensors pack glass powder in the insulation porcelain and melt and cool it to produce a high density solid sealing member within the gap between the sensor element and the insulation porcelain.

Typically, the sensor element and the insulation porcelain are made from zirconia and alumina, respectively. These materials are different in thermal expansion coefficient, thus causing the sensor element and the insulation porcelain to expand or shrink greatly at different rates, especially in a case where the gas sensor is installed in an extreme environment such as an exhaust system of an automotive engine in which the gas sensor experiences a great temperature change from a higher temperature level of exhaust gasses to a lower temperature level after a stop of the engine, which may result in formation of cracks in the sealing member in the insulation porcelain, thus leading to a decrease in degree of airtightness between the sensor element and the insulation porcelain.

In order to avoid such a problem, Japanese Patent First Publication No. 3-167461 (equivalent to U.S. Pat. No. 5,228,975) teaches limiting a difference in thermal expansion between a glass seal and a housing to a specific range. It is, however, difficult for the glass seal to absorb the expansion and shrinkage thereof completely. In order to alleviate such a problem, additional parts such as a spacer and a ceramic insulator are needed, which results in an increase in manufacturing costs. The structure of the above publication has also a problem that the expansion and shrinkage of the glass seal may cause the surface of the sensor element to be peeled off and the sensor element to be broken.

SUMMARY OF THE INVENTION

It is therefore a principal object of the invention to avoid the disadvantages of the prior art.

It is another object of the invention to provide an improved structure of a gas sensor which provides a mechanical seal required to keep a reference gas chamber and a gas chamber in the gas sensor airtight in an environment such as an automotive exhaust system subjected to a great temperature change.

According to the first aspect of the invention, there is provided a gas sensor which features a mechanical seal and which may be installed in an exhaust system of an internal combustion engine for air-fuel ratio control. The gas sensor comprises: (a) a hollow housing having a first and a second end portion; (b) a sensor element having a length which includes a first and a second portion; (c) a hollow insulating member disposed in the housing, retaining the sensor element therein; (d) a first cover installed on the first end portion of the housing to define a first chamber in which the first portion of the sensor element is exposed to a reference gas; (e) a second cover installed on the second end portion of the housing to define a second chamber in which the second portion of the sensor element is exposed to a gas to be measured; and (f) a glass sealing member disposed between an inner wall of the hollow insulating member and an outer wall of the sensor element to establish a hermetical seal between the first and second chamber. Differences in thermal expansion between the glass sealing member and the sensor element and between the sealing member and the insulation member are within a range of $\pm 3 \times 10^{-6}/°$ C.

In the preferred mode of the invention, a composition of the glass sealing member contains, as expressed by conversion to oxide, the following components:

$21.0 \pm 5\%$ by weight of $B_2O_3$, $34.6 \pm 5\%$ by weight of $ZnO$, $12.6 \pm 5\%$ by weight of $SiO_2$, $4.9 \pm 3\%$ by weight of $Al_2O_3$, $14.2 \pm 5\%$ by weight of $BaO$, and $12.7 \pm 5\%$ by weight of $MgO$.

Note that the conversion to oxides is accomplished, for example, by separating the glass sealing member into metallic elements and typical elements in any known manner and oxidize them under high temperatures.

The glass sealing member may be made by melting glass powder under high temperatures and solidifying it within the insulating member. The use of material of the sealing member containing $B_2O_3$ and $ZnO$ in the above weight percent range provides the differences in thermal expansion between the glass sealing member and the sensor element and between the glass sealing member and the insulation member which are within the range of $\pm 3 \times 10^{-6}/°$ C.

When the quantity of ZnO is less than the above weight percent range, it will degrade the crystallization of the glass sealing member, thus resulting in an increase in adverse effect of mechanical properties of non-crystallized glass components contained in the glass sealing member. This requires use of the gas sensor in a lower temperature environmental condition. Alternatively, when the quantity of ZnO is greater than the above weight percent range, it will promote the crystallization of the glass sealing member, thus resulting in a decrease in amount of the non-crystallized glass components. This decreases the adhesion of the glass sealing member to the sensor element and the insulating member made of alumina, thereby causing the degree of airtightness between the first and second chambers to be decreased.

When the quantity of BaO and MgO are within the above weight percent ranges, it enables desired ones of deposited crystals having coefficients of linear thermal expansion different from each other greatly to be balanced with each other, which allows the coefficient of linear thermal expansion of the glass sealing member to be brought close to that of the insulating member made of alumina.

When the quantity of $Al_2O_3$ is less than the above weight percent range, the crystallizing temperature of the glass sealing member will be close to the softening temperature and the glass transition point, so that the material of the glass sealing member is crystallized shortly after it is softened. This results in an increase in viscosity of the material of the glass sealing member, which causes the material to be solidified before filling up a gap between the sensor element and the insulating member, so that some leakage paths will be formed.

Alternatively, when the quantity of $Al_2O_3$ is greater than the above weight percent range, it arrests the crystallization of the material of the glass sealing member, thus resulting in an increase in adverse effect of mechanical properties of non-crystallized glass components contained in the glass sealing member. This requires use of the gas sensor in a lower temperature environmental condition.

The composition of the sealing member may alternatively contain, as expressed by conversion to oxide, the following groups of components:
(a) 21.0±5% by weight of $B_2O_3$,
  32.0±5% by weight of ZnO,
  19.0±5% by weight of $SiO_2$,
  12.0±5% by weight of BaO, and
  17.0±5% by weight of MgO.
(b) 26.0±3% by weight of $B_2O_3$,
  45.0±5% by weight of ZnO,
  14.0±3% by weight of $SiO_2$,
  7.5±3% by weight of BaO, and
  7.5±3% by weight of MgO.
(c) 24.0±5% by weight of $B_2O_3$,
  57.5±8% by weight of ZnO,
  11.0±5% by weight of $SiO_2$, and
  7.5±5% by weight of BaO.
(d) 22.6±5% by weight of $B_2O_3$,
  34.5±8% by weight of ZnO,
  12.8±5% by weight of $SiO_2$,
  11.5±5% by weight of BaO, and
  18.0±5% by weight of MgO.
(e) 19.0±5% by weight of $B_2O_3$,
  30.4±8% by weight of ZnO,
  16.0±5% by weight of $SiO_2$,
  5.0±3% by weight of $Al_2O_3$,
  20.0±5% by weight of BaO, and
  9.6±5% by weight of CaO.

The differences in thermal expansion between the sealing member and the sensor element and between the sealing member and the insulation member is preferably within a range of $\pm 2 \times 10^{-6}/°C$.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

Figure 2:
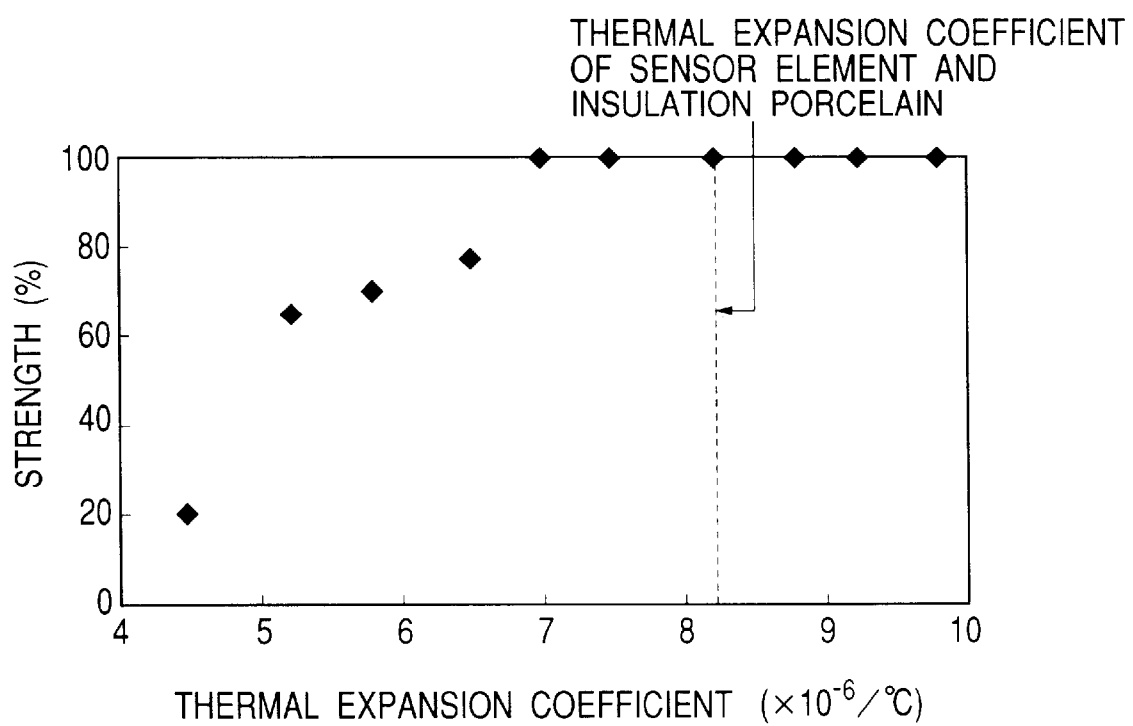

In the drawings:

FIG. 1 is a longitudinal sectional view which shows a gas sensor according to the first embodiment of the invention; and FIG. 2 is a graph which shows a relation between the coefficient of thermal expansion of a glass sealing member and the strength of an insulation porcelain and a sensor element.

DESCRIPTION OF THE PREFERRED EMBODIMENTS

Referring to the drawings, wherein like reference numbers refer to like parts in several views, particularly to FIG. 1, there is shown a gas sensor 1 according to the present invention which may be employed in an air-fuel ratio control system for automotive vehicles to measure the concentration of a gas component such as NOx, CO, HC, or $O_2$ contained in exhaust gasses of the engine.

The gas sensor 1 generally includes a sensor element 15, a first insulation porcelain 21, a second insulation porcelain 22, a hollow cylindrical housing 10, and an air cover 12. The sensor element 15 is made of a laminated plate. U.S. Pat. No. 5,573,650, issued on Nov. 12, 1996 to Fukaya et al. teaches a typical laminated sensor element, disclosure of which is incorporated herein by reference. The first insulation porcelain 21 is fitted within the housing 10 and holds therein the sensor element 15 through a glass sealing member 25. The glass sealing member 25 is made by melting a glass powder under high temperatures and cooling or solidifying it in a cylindrical chamber of the first insulation porcelain 21 to form a hermetic seal between an outer surface 150 of the sensor element 15 and an inner surface 210 of the cylindrical chamber of the first insulation porcelain 21. The glass sealing member 25 is preferably required to have a high degree of adhesion to the sensor element 15 and the first insulation porcelain 21. In order to meet this requirement, it is advisable that the glass sealing member 25 be made of a glass material which exhibits a flowability of 15 mm or more in a flow test. The flowability expresses the degree of flow of a pellet of glass which is 3 g in weight when it is fused on an alumina plate under the same conditions as those to make the glass sealing member 25 in the first insulation porcelain 21.

In a case of a crystallized glass which does not have a deformation-initiating temperature point at which the glass starts to be deformed in shape when re-heated and fused, a difference between the softening temperature and the crystallizing temperature will degrade the flowability thereof. Usually, the flowability of a glass material appears near the softening temperature and decreases greatly upon initiation of crystallization. The use of a glass material whose difference between the softening temperature and the crystallizing temperature is great enables the formation of a high-density hermetical seal between the first insulation porcelain 21 and the sensor element 15 without any gas-leakage gap therebetween. For example, in a case where the gas sensor 1 is installed in an exhaust system of automotive vehicles, the glass sealing member 25 is required to have a heat-resistance to 500 to 600° C. A sensing element made of zirconium oxide typically has a heat-resistance to about 1000° C. It is, thus, advisable that the glass sealing member 25 be made of a material which is fused and solidified in a range of 800 to 1000° C. Such a glass material usually has a crystallizing temperature of 700° C. or more. The material of the glass sealing member 25, thus, has a softening temperature that is different from the crystallizing temperature by 100%C or more.

Differences in coefficient of thermal expansion (i.e., the coefficient of linear thermal expansion) between the glass sealing member 25 and the first insulation porcelain 21 and between the glass sealing member 25 and the sensor element 15 are within a range of $\pm 3\times 10^{-6}/°$ C., preferably $\pm 2\times 10^{-6}/°$ C., and more preferably $\pm 1\times 10^{-6}/°$ C. which will be discussed in detail later with reference to Table 1.

The second insulation porcelain 22 is mounted on the first insulation porcelain 21 and surrounds a base portion of the sensor element 15. The air cover 12 is installed at an end thereof on the housing 10 and surrounds the second insulation porcelain 22 to define an air chamber 142. The second insulation porcelain 22 is formed by a hollow cylindrical insulating member and has disposed therein four leads 16 (only two are shown for the simplicity of illustration) each of which is made of a wire folded elastically to make an electric contact at one end with an electrode terminal (not shown) formed on the sensor element 15. The leads 16 extend at the other end through holes formed in an end of the second insulation porcelain 22 and connect with four leads 18 through connectors 17, respectively, for transmission of sensor signals between the sensor element 15 and an external device and supply of electric power to a heater installed on the sensor element 15.

The gas sensor 1 also includes a protective cover assembly 13 consisting of an outer cover 131 and an inner cover 132. The protective cover assembly 13 is installed in a head of the housing 10 to define a gas chamber 141 into which a gas to be measured is admitted through gas holes 130 formed in the outer and inner covers 131 and 132.

The first insulation porcelain 21 has an annular shoulder 211. The shoulder 211 has a tapered surface and is placed through a metal packing ring 11 on a seat surface 103 of an annular shoulder 101 formed on an inner wall of the housing 10. Specifically, a gap between the housing 10 and the first insulation porcelain 21 is sealed hermetically by the metal packing ring 11 to keep the air chamber 142 and the gas chamber 141 airtight. The metal packing ring 11 is made of a pure nickel having a 99% purity. The first insulation porcelain 21 is made of an alumina ceramic having a 98% purity whose thermal expansion coefficient is $7.8\times 10^{-6}/°$ C. in a range of room temperature to 550° C.

The air cover 12 is, as described above, fitted on the base end of the housing 10. An outer cover 121 is provided around the air cover 12 and staked or crimped to retain a water-repellent filter 122 on the periphery of the air cover 12. The air cover 12 and the outer cover 121 have formed therein air vents 120 through which air is admitted into the air chamber 142. The air cover 12 has a shoulder 129 to define a small-diameter portion and a large-diameter portion. A disc spring 220 is disposed between the shoulder 129 and an end of the second insulation porcelain 22 to elastically urge the second insulation porcelain 22 into constant engagement with the first insulation porcelain 21 to increase the degree of airtightness provided by the metal packing ring 11. An insulating holder 23 made of rubber is disposed inside the small-diameter portion of the air cover 12.

The sensor element 15, as described above, has a heater built therein which heats the sensor element 15 up to a temperature required for the sensor element 15 to be sensitive to a gas to be measured correctly. The sensor element 15 has formed thereon four electrode terminals two of which are used for outputting sensor signals and the others for supply of electric power to the heater. The electrode terminals are connected electrically with ends of the leads 16 in an illustrated manner, respectively. The leads 16 extend through the holes formed in the end wall of the second insulation porcelain 22 and are inserted into the connectors 17, respectively. The connectors 17 are coupled with the leads 18 retained in holes formed in the insulating holder 23. This structure is not essential part of this invention and known in the art, and explanation thereof in detail will be omitted here.

The sensor element 15 is, as described above, made of a lamination of a zirconia ceramic (e.g., an oxygen nonconductive zirconia) and an alumina ceramic as a whole and has at the outer surface 150 a thermal expansion coefficient of $7.8\times 10^{-6}/°$ C. in a range of room temperature to 550° C. which is identical with that of the first insulation porcelain 21.

The glass sealing member 25 is, as described above, disposed within the first insulation porcelain 21 to seal the gap between the outer surface 150 of the sensor element 15 and the inner surface 210 of the first insulation porcelain 21. If expressed by conversion to oxides, a composition of the glass sealing member 25 is made up of 21.0±5% by weight of $B_2O_3$, 34.6±5% by weight of ZnO, 12.6±5% by weight of $SiO_2$, 4.9±3% by weight of $Al_2O_3$, 14.2±5% by weight of BaO, and 12.7±5% by weight of MgO. Note that the conversion to oxides is accomplished, for example, by separating the glass sealing member 25 into metallic elements and typical elements in any known manner and oxidize them under high temperatures.

Specifically, a crystallized glass composition of the glass sealing member 25 contains the following components:
No. 1 $2ZnO.SiO_2$
No. 2 $ZnO.B_2O_3$
No. 3 $2MgO.B_2O_3$
No. 4 $BaO.2MgO.2SiO_2$
No. 5 $BaO.Al_2O_3.2SiO_2$ The above components occupy 80% of the whole of the glass sealing member 25. The remainder consists essentially of noncrystal components and occupies about 20% of the whole of the glass sealing member 25. The noncrystal components are complexes containing one or some of the above components No. 1 to No. 5 which are difficult to identify.

The above composition of the glass sealing member 25 provides the differences in coefficient of thermal expansion between the glass sealing member 25 and the first insulation porcelain 21 and between the glass sealing member 25 and the sensor element 15 within the range of $\pm 3.0\times 10^{-6}/°$ C. and also improves the wettability and flowability of the glass sealing member 25 with respect to the first insulation porcelain 21 and the sensor element 15, thus resulting in an increase in degree of airtightness produced by the glass sealing member 25.

For characteristics of the glass sealing member 25, the glass transition point is 560 to 580° C. The softening point is 635 to 655° C. The crystallizing temperature is 735 to 765° C. The sealing temperature at which a glass powder is melted to produce the glass sealing member 25 is 830 to 950° C. The coefficient of linear thermal expansion may be selected from 7.0 to $8.2\times 10^{-6}/°$ C. in a range of room temperature to 550° C. depending upon conditions for producing the glass sealing member 25 in the first insulation porcelain 21.

The inventors of this application prepared a plurality of sensors in which equivalents of the sensor element 15 are installed in equivalents of the insulation porcelain 21, and gaps therebetween are sealed hermetically by equivalents of the glass sealing member 25 having different coefficients of thermal expansion and pressed the equivalents of the insulation porcelain 21 through equivalents of the insulation porcelain 22 to measure applied pressures initiating formation of cracks in the equivalents of the insulation porcelain 21 or the glass sealing member 25. The results of tests are shown in a graph of FIG. 2. "Strength" as indicated on the ordinate axis expresses a value of (applied pressure having induced crack in sensor with glass sealing member/applied pressure having induced crack in sensor not using glass sealing member) ×100%. If the glass sealing member 25 is smaller in coefficient of thermal expansion than the insulation porcelain 21, the alumina-made insulation porcelain 21 undergoes a tensile stress after the glass sealing member 25 is formed, thereby causing the strength of the insulation porcelain 21 to be decreased as compared with when the glass sealing member 25 is not installed.

The graph of FIG. 2 shows that when a difference in coefficient of thermal expansion between the glass sealing member 25 and the insulation porcelain 21 or between the glass sealing member 25 and the sensor element 15 is greater than $3 \times 10^{-6}/°$ C., and the coefficient of thermal expansion of the glass sealing member 25 is below $5.2 \times 10^{-6}/°$ C., it will result in a great decrease in the strength. Specifically, when the coefficient of thermal expansion of the glass sealing member 25 is smaller than those of the first insulation porcelain 21 and the sensor element 15 by $3 \times 10^{-6}/°$ C., it will cause the residual stress in the first insulation porcelain 21 arising from melting and solidification of glass powder to make the glass sealing member 25 to increase, thus resulting in an increase in pressure to widen the inner chamber of the first insulation porcelain 21 which may lead to cracking in the first insulation porcelain 21 to produce leakage paths when the first insulation porcelain 21 is subjected to a great thermal impact in an environment such as an automotive exhaust system. The same is true for the sensor element 15, which may lead to breakage of the electrodes formed on the sensor element 15.

Although not illustrated in FIG. 2, it has also been found that when the coefficient of thermal expansion of the glass sealing member 25 is greater than those of the insulation porcelain 21 and the sensor element 15 by $3 \times 10^{-6}/°$ C., the strength of the insulation porcelain 25 does not decrease, but contact surfaces between the glass sealing member 25 and the insulation porcelain 21 and between the glass sealing member 25 and the sensor element 15 peel off due to a difference in degree of shrinkage therebetween when the glass powder is melted and crystallized to make the glass sealing member 25, thus resulting in leakage paths communicating between.

Quick thermal impact tests were performed by heating gas sensors equipped with equivalents of the sensor element 15, equivalents of the insulation porcelain 21, and equivalents of the glass sealing member 25 having coefficients of thermal expansion, as shown in Table 1 below, and water-cooling them at rates of 100° C./sec., 150° C./sec. and 200° C./sec. to check formation of cracks in the sensor elements, the insulation porcelains, and the glass sealing members.

TABLE 1

| No. | Thermal expansion coefficient | Difference | 100° C./sec. | 150° C./sec. | 200° C./sec. |
|---|---|---|---|---|---|
| A | $5.2 \times 10^{-6}$ | $-3.0 \times 10^{-6}$ | ○ | ○ | △ |
| B | $6.7 \times 10^{-6}$ | $-1.5 \times 10^{-6}$ | ○ | ○ | △ |
| C | $7.2 \times 10^{-6}$ | $-1.0 \times 10^{-6}$ | ○ | ○ | ○ |
| D | $7.6 \times 10^{-6}$ | $-0.6 \times 10^{-6}$ | ○ | ○ | ○ |
| E | $8.0 \times 10^{-6}$ | $-0.3 \times 10^{-6}$ | ○ | ○ | ○ |
| F | $8.5 \times 10^{-6}$ | $+0.3 \times 10^{-6}$ | ○ | ○ | ○ |

"○" indicates the absence of cracks.
"△" indicates the presence of cracks in any of the insulation porcelains, the glass sealing members, and the sensor elements.

Table 1 shows that the glass sealing members having the same coefficient of thermal expansion as that of the glass sealing member 25 do not experience the formation of cracks even when they are cooled at the rate of 150° C./sec., and that when differences in coefficient of thermal expansion between the glass sealing members and the sensor elements and between the glass sealing members and the insulation porcelains are within $1.0 \times 10^{-6}/°$ C., the glass sealing member 25 do not experience the formation of cracks even when they are cooled at the rate of 200° C./sec.

The composition of the glass sealing member 25 may alternatively contain one of the following groups (a) to (f):

(a) 21.0±5% by weight of $B_2O_3$, 32.0±5% by weight of ZnO, 19.0±5% by weight of $SiO_2$, 12.0±5% by weight of BaO, and 17.0±5% by weight of MgO.

(b) 26.0±3% by weight of $B_2O_3$, 45.0±5% by weight of ZnO, 14.0±3% by weight of $SiO_2$, 7.5±3% by weight of BaO, and 7.5±3% by weight of MgO, (c) 21.0±5% by weight of $B_2O_3$, 34.6±5% by weight of ZnO, 12.6±5% by weight of $SiO_2$, 4.9.0±3% by weight of $Al_2O_3$, 14.2±5% by weight of BaO, and 12.7±5% by weight of MgO, (d) 24.0±5% by weight of $B_2O_3$, 57.5±8% by weight of ZnO, 11.0±5% by weight of $SiO_2$, and 7.5±5% by weight of BaO, (e) 22.6±5% by weight of $B_2O_3$, 34.5±8% by weight of ZnO, 12.8±5% by weight of $SiO_2$, 11.5±5% by weight of BaO, and 18.0±5% by weight of MgO, and (f) 19.0±5% by weight of $B_2O_3$, 30.4±8% by weight of ZnO, 16.0±5% by weight of $SiO_2$, 5.0±3% by weight of $Al_2O_3$, 20.0±5% by weight of BaO, and 9.6±5% by weight of CaO.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. For example, the sensor element 15 is made of a known cup-shaped solid electrolyte body.

What is claimed is:

1. A gas sensor comprising:

a hollow housing having a first and a second end portion;

a sensor element having a length which includes a first and a second portion;

a hollow insulating member disposed in said housing, retaining said sensor element therein;

a first cover installed on the first end portion of said housing to define a first chamber in which the first portion of said sensor element is exposed to a reference gas;

a second cover installed on the second end portion of said housing to define a second chamber in which the second portion of said sensor element is exposed to a gas to be measured; and a glass sealing member disposed between an inner wall of said hollow insulating member and an outer wall of said sensor element to establish a hermetical seal between the first and second chamber, wherein differences in thermal expansion between said glass sealing member and said sensor element and between said glass sealing member and said hollow insulating member are within a range of $\pm 1 \times 10^{-6}/°$ C.

2. A gas sensor as set forth in claim 1, wherein a composition of said glass sealing member contains, as expressed by conversion to oxide, the following components:

21.0±5% by weight of $B_2O_3$,
34.6±5% by weight of ZnO,
12.6±5% by weight of $SiO_2$,
4.9±3% by weight of $Al_2O_3$,
14.2±5% by weight of BaO, and
12.7±5% by weight of MgO.

3. A gas sensor as set forth in claim 1, wherein a composition of said glass sealing member contains, as expressed by conversion to oxide, the following components:

21.0±5% by weight of $B_2O_3$,
32.0±5% by weight of ZnO,
19.0±5% by weight of $SiO_2$,
12.0±5% by weight of BaO, and
17.0±5% by weight of MgO.

4. A gas sensor as set forth in claim 1, wherein a composition of said glass sealing member contains, as expressed by conversion to oxide, the following components:

26.0±3% by weight of $B_2O_3$,
45.0±5% by weight of ZnO,
14.0±3% by weight of $SiO_2$,
7.5±3% by weight of BaO, and
7.5±3% by weight of MgO.

5. A gas sensor as set forth in claim 1, wherein a composition of said glass sealing member contains, as expressed by conversion to oxide, the following components:

24.0±5% by weight of $B_2O_3$,
57.5±8% by weight of ZnO,
11.0±5% by weight of $SiO_2$, and
7.5±5% by weight of BaO.

6. A gas sensor as set forth in claim 1, wherein a composition of said glass sealing member contains, as expressed by conversion to oxide, the following components:

22.6±5% by weight of $B_2O_3$,
34.5±8% by weight of ZnO,
12.8±5% by weight of $SiO_2$,
11.5±5% by weight of BaO, and
18.0±5% by weight of MgO.

7. A gas sensor as set forth in claim 1, wherein a composition of said glass sealing member contains, as expressed by conversion to oxide, the following components:

19.0±5% by weight of $B_2O_3$,
30.4±8% by weight of ZnO,
16.0±5% by weight of $SiO_2$,
5.0±3% by weight of $Al_2O_3$,
20.0±5% by weight of BaO, and
9.6±5% by weight of CaO.

8. A gas sensor as set forth in claim 1, wherein a gap between said insulating member and said sensor element is sealed hermetically only by said glass sealing member.

9. A gas sensor as set forth in claim 1, installed in an internal combustion engine.

10. A gas sensor as set forth in claim 9, installed in the exhaust system of the engine combustion engine for air-fuel ratio control.

11. A gas sensor as set forth in claim 1, wherein the glass sealing member is made of a glass material which exhibits a flowability of 15 mm or more.

12. A gas sensor as set forth in claim 1, wherein the material of the glass sealing member has a softening temperature that differs from its crystallizing temperature by 100° C. or more.

13. A gas sensor as set forth in claim 1, wherein the coefficient of linear thermal expansion of the glass sealing member is from 7.0 to $8.2 \times 10^{-6}/°$ C. in a range of room temperature to 550° C.

* * * * *